United States Patent
Tang et al.

(10) Patent No.: US 7,919,627 B2
(45) Date of Patent: Apr. 5, 2011

(54) PROCESSES FOR THE PREPARATION OF HYDROXYLAMINES

(75) Inventors: Datong Tang, Watertown, MA (US); Yao-Ling Qiu, Andover, MA (US); Heejin Kim, Allston, MA (US); Yat Sun Or, Watertown, MA (US); Zhe Wang, Hockessin, DE (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 18 days.

(21) Appl. No.: 12/135,299

(22) Filed: Jun. 9, 2008

(65) Prior Publication Data

US 2008/0242865 A1  Oct. 2, 2008

Related U.S. Application Data

(63) Continuation-in-part of application No. 11/205,764, filed on Aug. 17, 2005, now Pat. No. 7,538,225.

(51) Int. Cl.
*C07D 401/04* (2006.01)
(52) U.S. Cl. .................................................. 546/275.4
(58) Field of Classification Search ............. 546/275.4
See application file for complete search history.

(56) References Cited

U.S. PATENT DOCUMENTS

| 7,135,573 B2 * | 11/2006 | Kim et al. ............ 546/275.4 |
| 7,189,704 B2 | 3/2007 | Niu et al. |
| 7,273,853 B2 | 9/2007 | Or et al. |
| 7,384,922 B2 | 6/2008 | Wang et al. |
| 7,538,225 B2 | 5/2009 | Tang et al. |
| 2007/0244160 A1 | 10/2007 | Or et al. |
| 2008/0262208 A1 | 10/2008 | Wang et al. |

* cited by examiner

*Primary Examiner* — Patricia L Morris
(74) *Attorney, Agent, or Firm* — Edgar W. Harlan; Carolyn S. Elmore; Elmore Patent Law Group PC

(57) ABSTRACT

The present invention relates generally to novel methods for the synthesis of O-(6-pyrazol-1-yl-pyridin-3-ylmethyl)-hydroxylamine which is an essential reagent in the synthesis of one of the bridged erythromycin derivatives and their respective pharmaceutically acceptable salts in PCT Application WO 03/097659 A1. In particular, the present invention relates to processes and intermediates for the preparation of a compound of formula (Ia):

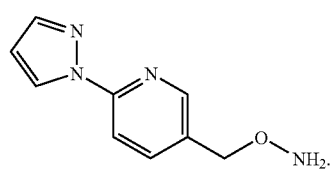

(Ia)

10 Claims, No Drawings

PROCESSES FOR THE PREPARATION OF HYDROXYLAMINES

RELATED APPLICATIONS

This application is a divisional application of U.S. application Ser. No. 11/205,764, filed on Aug. 17, 2005, which claims the benefit of U.S. Provisional Application No. 60/676,727, filed on May 2, 2005 and U.S. Provisional Application No. 60/696,622, filed on Jul. 5, 2005. The entire teachings of the above applications are incorporated herein by reference.

TECHNICAL FIELD

The present invention relates generally to the processes and intermediates useful in the preparation O-(6-pyrazol-1-yl-pyridin-3-ylmethyl)-hydroxylamine which is a reagent in the synthesis of certain bridged erythromycin and ketolide derivatives described in U.S. Pat. No. 6,878,691, U.S. Pat Pub. No. 2005037982 and PCT Application WO 03/097659 A1.

BACKGROUND OF THE INVENTION

Macrolide antibiotics play a therapeutically important role, particularly with the emergence of new pathogens. Structural differences are related to the size of the lactone ring and to the number and nature (neutral or basic) of the sugars. Macrolides are classified according to the size of the lactone ring (12, 14, 15 or 16 atoms). The macrolide antibiotic family (14-, 15- and 16-membered ring derivatives) shows a wide range of characteristics (antibacterial spectrum, side-effects and bioavailability). Among the commonly used macrolides are erythromycin, clarithromycin, and azithromycin. Macrolides possessing a 3-oxo moiety in place of the 3-cladinose sugar are known as ketolides and have shown enhanced activity towards gram-negative bacteria and macrolide resistant gram-positive bacteria. The search for macrolide compounds which are active against $MLS_B$-resistant strains ($MLS_B$=Macrolides-Lincosamides-type B Streptogramines) has become a major goal, together with retaining the overall profile of the macrolides in terms of stability, tolerance and pharmacokinetics.

Recently PCT Application WO 03/095466 A1, published Nov. 20, 2003 and PCT Application WO 03/097659 A1, published Nov. 27, 2003 disclose a series of bicyclic erythromycin derivatives.

SUMMARY OF THE INVENTION

The present invention provides methods for preparing compounds of Formula I:

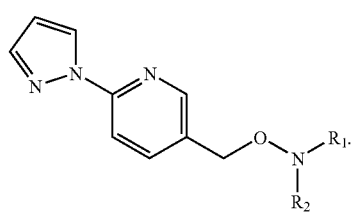

A most preferred embodiment of a compound of formula I is O-(6-pyrazol-1-yl-pyridin-3-ylmethyl)-hydroxylamine having the formula Ia:

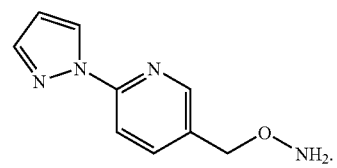

In one embodiment of the invention, pyridyl derivatives of formulae I are reacted with pyrazole in the presence of acids, bases or metallic catalysts. The invention further relates to increasing product yield and decreasing process steps for intermediate and large scale production O-(6-pyrazol-1-yl-pyridin-3-ylmethyl)-hydroxylamine. Compounds of Formula I and particularly, O-(6-pyrazole-1-yl-pyridin-3-ylmethyl)-hydroxylamine is particularly useful as a reagent in the synthesis of EP13420 which has the following formula:

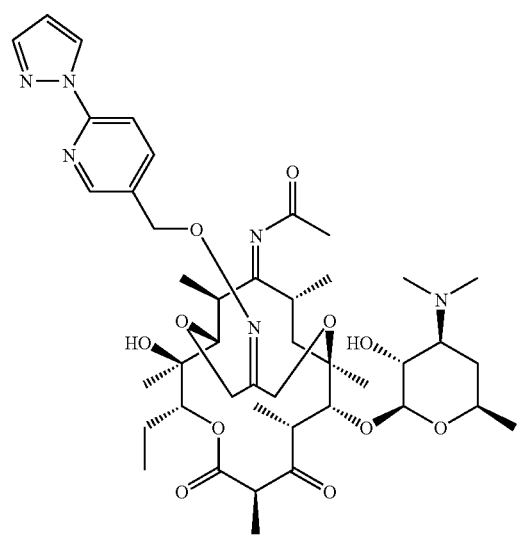

DETAILED DESCRIPTION OF THE INVENTION

In a first embodiment, the present invention provides a process for the preparation of compounds of formulae (I);

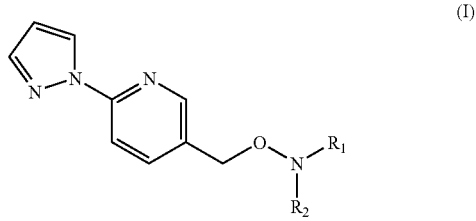

wherein $R_1$ and $R_2$ are each independently selected from:
(a) hydrogen; or
(b) $NH_2$;

or one of $R_1$ or $R_2$ is a hydrogen and the other is selected from:
(a) $C(O)R_3$, where $R_3$ is $C_1$-$C_6$ alkyl, optionally substituted with one or more substituents selected from aryl, substituted aryl, heteroaryl, or substituted heteroaryl;
(b) $C(O)OR_3$, where $R_3$ is as previously defined; or.

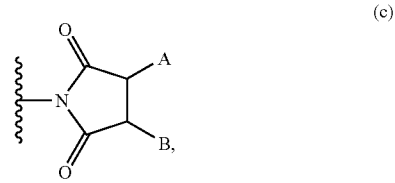
(c)

wherein A and B are each independently hydrogen, a substituted or unsubstituted aliphatic group, a substituted or unsubstituted cyclic group, a substituted or unsubstituted heterocyclic group, a substituted or unsubstituted aryl group, a substituted or unsubstituted alicyclic group, or a substituted or unsubstituted heteroaryl group; or A and B taken together with the carbon to which they are attached form a cyclic moiety selected from: aryl, substituted aryl, heterocyclic, substituted heterocyclic, alicyclic, or substituted alicyclic;
alternatively, $R_1$ and $R_2$ are taken together with the nitrogen atom to which they are attached to form $N=C(R_4)(R_5)$, where $R_4$ and $R_5$ are each independently selected from a substituted or unsubstituted aliphatic group, a substituted or unsubstituted cyclic group, a substituted or unsubstituted heterocyclic group, a substituted or unsubstituted aryl group, a substituted or unsubstituted alicyclic group, or a substituted or unsubstituted heteroaryl group;
said process comprising one or more of the following steps:
(1) treating 2-chloro-5-chloromethyl-pyridine with compounds of formula $R_1R_2NOH$ wherein R1 and R2 are as previously defined in the presence of base to yield compounds of formulae (II):

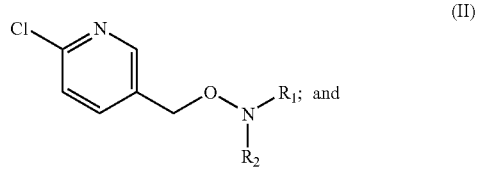
(II)

(2) reacting pyrazole with compound of formulae (II) in the presence of acid, base and metallic catalyst to provide compound of formula (I):

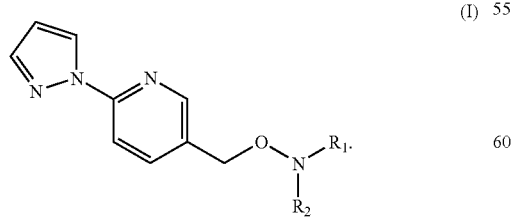
(I)

Optionally, the process may further comprise the step of hydrolyzing the compound of formula I with a base or an acid in a protogenic organic solvent or aqueous solution, to yield a preferred compound of the invention, O-(6-pyrazol-1-yl-pyridin-3-ylmethyl)-hydroxylamine, having the formulae (Ia):

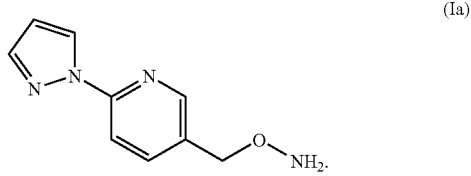
(Ia)

In a second embodiment, the present invention provides a process for the preparation of a compound of formulae (I);

(I)

wherein $R_1$ and $R_2$ are each independently selected from
(a) hydrogen; or
(b) $NH_2$;
or one of $R_1$ or $R_2$ is a hydrogen and the other is selected from:
(a) $C(O)R_3$, where $R_3$ is $C_1$-$C_6$ alkyl, optionally substituted with one or more substituents selected from aryl, substituted aryl, heteroaryl, or substituted heteroaryl;
(b) $C(O)OR_3$, where $R_3$ is as previously defined; or (c)

wherein A and B are each independently hydrogen, a substituted or unsubstituted aliphatic group, a substituted or unsubstituted cyclic group, a substituted or unsubstituted heterocyclic group, a substituted or unsubstituted aryl group, a substituted or unsubstituted alicyclic group, or a substituted or unsubstituted heteroaryl group; or A and B taken together with the carbon to which they are attached to form a cyclic moiety selected from: aryl, substituted aryl, heterocyclic, substituted heterocyclic, alicyclic, or substituted alicyclic;
alternatively, $R_1$ and $R_2$ are taken together with the nitrogen atom to which they are attached to form $N=C(R_4)(R_5)$, where $R_4$ and $R_5$ are each independently selected from a substituted or unsubstituted aliphatic group, a substituted or unsubstituted cyclic group, a substituted or unsubstituted heterocyclic group, a substituted or unsubstituted aryl group, a substituted or unsubstituted alicyclic group, or a substituted or unsubstituted heteroaryl group;

said process comprising one or more of the following steps:
(1) treating (6-chloro-pyridin-3-yl)-methanol with a suitable hydroxyl protecting reagent to form compounds of formulae (IV):

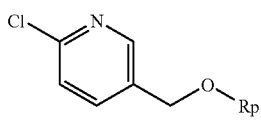
(IV)

where Rp is a hydroxyl protecting group;
(2) reacting pyrazole with compounds of formulae (IV) in the presence of base to give compound of the following formula V:

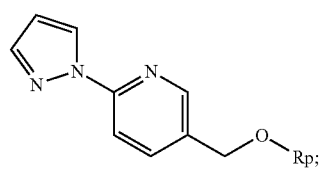
(V)

(3) deprotecting the hydroxyl protecting group of formula (V) and halogenating the corresponding compound with a chlorinating reagent to provide a compound of formula (VI):

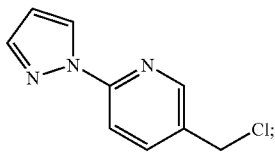
(VI)

(4) treating compounds of formulae (VI) with compounds of formula $R_1R_2NOH$ wherein R1 and R2 are as previously defined, in the presence of base, followed by hydrolysis to provide compounds of formula (I).

Optionally, the process may further comprise the step of hydrolyzing the compound of formula I with a base or an acid in a protogenic organic solvent or aqueous solution, to yield a preferred compound of the invention, O-(6-pyrazol-1-yl-pyridin-3-ylmethyl)-hydroxylamine, having the formulae (Ia):

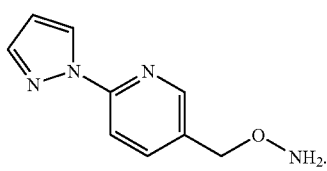
Ia

In yet another embodiment of the invention a process is provided that comprises one or more of the following steps:
(1) treating (6-chloro-pyridin-3-yl)-methanol with pyrazole in the presence of any of the following: an acid catalyst in organic solvent, preferably in an aprotic solvent; a neat organic acid; or a base with a catalyst such as copper(I) salt or other transition metal derivatives combined with 1,2-diamino derivatives, preferably in an aprotic solvent; to form a compound of formula III, (6-Pyrazole-1-yl-pyrind-3-yl)-methanol:

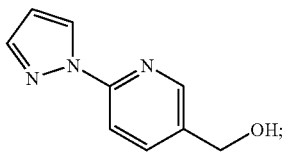

(2) halogenating the compound of formula III with a chlorinating reagent to provide a compound of formula (VI):

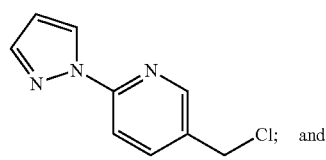
(VI)

(3) reacting at least one compound of the formula $R_1R_2NOH$ wherein $R_1$ and $R_2$ are as previously defined, with the compound of formula VI to form a compound of formula I.

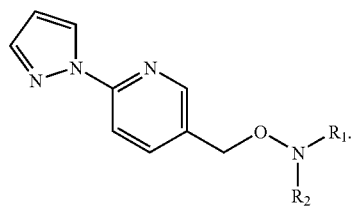
I

Optionally, the process may further comprise the step of hydrolyzing the compound of formula I with a base or an acid in a protogenic organic solvent or aqueous solution, to yield a preferred compound of the invention, O-(6-pyrazol-1-yl-pyridin-3-ylmethyl)-hydroxylamine, having the formulae (Ia):

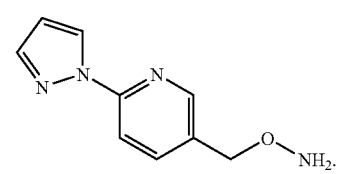
Ia

The above processes, as well as other processes depicted in this application react either a pyrazole, hydroxylamine or other compound with a chloropyridine or a substituted chloroalkane (e.g., a substituted pyridinylmethyl chloride). In these reactions, the chloride acts as a leaving group. In yet another set of embodiments of the invention, other leaving groups can be used in place of the chlorine. Examples of leaving groups include, without limitation, halo groups, e.g., bromine, or sulfonates, e.g., tosylate, mesylate, nosylate, and triflate. In this embodiment, the Cl of the formula set forth above can be replaced with a LG wherein LG is a leaving group.

DEFINITIONS

Listed below are definitions of various terms used to describe this invention. These definitions apply to the terms as they are used throughout this specification and claims, unless otherwise limited in specific instances, either individually or as part of a larger group.

An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

Suitable aliphatic or aromatic substituents include, but are not limited to, —F, —Cl, —Br, —I, —OH, protected hydroxy, aliphatic ethers, aromatic ethers, oxo, —NO$_2$, —CN, —C$_1$-C$_{12}$-alkyl optionally substituted with halogen (such as perhaloalkyls), C$_2$-C$_{12}$-alkenyl optionally substituted with halogen, —C$_2$-C$_{12}$-alkynyl optionally substituted with halogen, —NH$_2$, protected amino, —NH—C$_1$-C$_{12}$-alkyl, —NH—C$_2$-C$_{12}$-alkenyl, —NH—C$_2$-C$_{12}$-alkynyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkynyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkynyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkynyl, —CONH—C$_3$-C$_{12}$-cycloalkyl, —CONH-aryl, —CONH-heteroaryl, —CONH-heterocycloalkyl, —CO$_2$—C$_1$-C$_{12}$-alkyl, —CO$_2$—C$_2$-C$_{12}$-alkenyl, —CO$_2$—C$_2$-C$_{12}$-alkynyl, —CO$_2$—C$_3$-C$_{12}$-cycloalkyl, —CO$_2$-aryl, —CO$_2$-heteroaryl, —CO$_2$-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkynyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkynyl, —OCONH—C$_3$-C$_{12}$-cycloalkyl, —OCONH-aryl, —CONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkynyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$-C$_{12}$-alkyl, —NHC(O)NH—C$_2$-C$_{12}$-alkenyl, —NHC(O)NH—C$_2$-C$_{12}$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$-C$_{12}$-alkyl, —NHC(S)NH—C$_2$-C$_{12}$-alkenyl, —NHC(S)NH—C$_2$-C$_{12}$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$-C$_{12}$-alkyl, —NHC(NH)NH—C$_2$-C$_{12}$-alkenyl, —NHC(NH)NH—C$_2$-C$_{12}$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, NHC(NH)—C$_1$-C$_{12}$-alkyl, —NHC(NH)—C$_2$-C$_{12}$-alkenyl, —NHC(NH)—C$_2$-C$_{12}$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkynyl, —S(O)—C$_3$-C$_{12}$-cycloalkyl, —S(O)-aryl, —S(O)-heteroaryl, —S(O)-heterocycloalkyl-SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkynyl, —S—C$_3$-C$_{12}$-cycloalkyl, —S-aryl, —S-heteroaryl, —S-heterocycloalkyl, or methylthiomethyl. It is understood that the aryls, heteroaryls, alkyls and the like can be further substituted.

The terms "C$_2$-C$_{12}$ alkenyl" or "C$_2$-C$_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, alkadienes and the like.

The term "substituted alkenyl," as used herein, refers to a "C$_2$-C$_{12}$ alkenyl" or "C$_2$-C$_6$ alkenyl" group as previously defined, substituted by one, two, three or more aliphatic substituents.

The terms "C$_2$-C$_{12}$ alkynyl" or "C$_2$-C$_6$ alkynyl," as used herein, denote a monovalent group derived from a hydrocarbon moiety containing from two to twelve or two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "substituted alkynyl," as used herein, refers to a "C$_2$-C$_{12}$ alkynyl" or "C$_2$-C$_6$ alkynyl" group as previously defined, substituted by one, two, three or more aliphatic substituents.

The term "C$_1$-C$_6$ alkoxy," as used herein, refers to a C$_1$-C$_6$ alkyl group, as previously defined, attached to the parent molecular moiety through an oxygen atom. Examples of C$_1$-C$_6$-alkoxy include, but are not limited to, methoxy, ethoxy, propoxy, isopropoxy, n-butoxy, sec-butoxy, tert-butoxy, n-pentoxy, neopentoxy and n-hexoxy.

The terms "halo" and "halogen," as used herein, refer to an atom selected from fluorine, chlorine, bromine and iodine.

The terms "aryl" or "aromatic" as used herein, refer to a mono- or bicyclic carbocyclic ring system having one or two aromatic rings including, but not limited to, phenyl, naphthyl, tetrahydronaphthyl, indanyl, idenyl and the like.

The terms "substituted aryl" or "substituted aromatic," as used herein, refer to an aryl or aromatic group substituted by one, two, three or more aromatic substituents.

The term "arylalkyl," as used herein, refers to an aryl group attached to the parent compound via a C$_1$-C$_3$ alkyl or C$_1$-C$_6$ alkyl residue. Examples include, but are not limited to, benzyl, phenethyl and the like.

The term "substituted arylalkyl," as used herein, refers to an arylalkyl group, as previously defined, substituted by one, two, three or more aromatic substituents.

The terms "heteroaryl" or "heteroaromatic," as used herein, refer to a mono-, bi- or tri-cyclic aromatic radical or ring having from five to ten ring atoms of which at least one ring atom is selected from S, O and N; zero, one or two ring atoms are additional heteroatoms independently selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The heteroaromatic ring may be bonded to the chemical structure through a carbon or hetero atom.

The terms "substituted heteroaryl" or "substituted heteroaromatic," as used herein, refer to a heteroaryl or heteroaromatic group, substituted by one, two, three, or more aromatic substituents.

The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl.

The term "substituted alicyclic," as used herein, refers to an alicyclic group substituted by one, two, three or more aliphatic substituents.

The term "heterocyclic," as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl.

The term "substituted heterocyclic," as used herein, refers to a heterocyclic group, as previously defined, substituted by one, two, three or more aliphatic substituents.

The term "heteroarylalkyl," as used herein, to an heteroaryl group attached to the parent compound via a $C_1$-$C_3$ alkyl or $C_1$-$C_6$ alkyl residue. Examples include, but are not limited to, pyridinylmethyl, pyrimidinylethyl and the like.

The term "substituted heteroarylalkyl," as used herein, refers to a heteroarylalkyl group, as previously defined, substituted by independent replacement of one, two, or three or more aromatic substituents.

The term "alkylamino" refers to a group having the structure —NH($C_1$-$C_{12}$ alkyl).

The term "dialkylamino" refers to a group having the structure —N($C_1$-$C_{12}$ alkyl) ($C_1$-$C_{12}$ alkyl), where $C_1$-$C_{12}$ alkyl is as previously defined. Examples of dialkylamino are, but not limited to, dimethylamino, diethylamino, methylethylamino, piperidino, and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —C(O)NH($C_1$-$C_{12}$ alkyl) or —C(O)N($C_1$-$C_{12}$ alkyl)($C_1$-$C_{12}$ alkyl), —C(O)NH$_2$, NHC(O)($C_1$-$C_{12}$ alkyl), N($C_1$-$C_{12}$ alkyl)C(O)($C_1$-$C_{12}$ alkyl) and the like.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "protected hydroxy," as used herein, refers to a hydroxy group protected with a hydroxy protecting group, as defined above, including benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al, Vol. II, in the *Techniques of Chemistry Series*, John Wiley & Sons, NY, 1986.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

The term "oxidizing agent(s)," as used herein, refers to reagents useful for oxidizing the 3-hydroxyl of the macrolide ring to the 3-carbonyl. Oxidizing agents suitable in the present process are either Swern oxidation reagents (dimethyl sulfoxide and an electrophilic compound selected from dicyclohexylcarbodiimide, acetic anhydride, trifluoroacetic anhydride, oxalyl chloride, or sulfur trioxide), Dess Martin oxidation reagents, or Corey-Kim oxidation reagents. A preferred method of oxidation is the use of the Corey-Kim oxidation reagents N-chlorosuccinimide-dimethyl sulfide complex.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

Prodrugs include compounds wherein an amino acid residue, or a polypeptide chain of two or more (e.g., two, three or four) amino acid residues is covalently joined through an amide or ester bond to a free amino, hydroxy or carboxylic acid group of a bridged erythromycin or ketolide derivative synthesized using the reagents prepared in accordance with the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

Suitable concentrations of reactants used in the synthesis processes of the invention are 0.01M to 10M, typically 0.1M to 1M. Suitable temperatures include −10° C. to 250° C., typically −78° C. to 150° C., more typically −78° C. to 100° C., still more typically 0° C. to 100° C. Reaction vessels are preferably made of any material which does not substantial interfere with the reaction. Examples include glass, plastic, and metal. The pressure of the reaction can advantageously be operated at atmospheric pressure. The atmospheres include, for example, air, for oxygen and water insensitive reactions, or nitrogen or argon, for oxygen or water sensitive reactions.

The term "in situ," as used herein, refers to use of an intermediate in the solvent or solvents in which the intermediate was prepared without removal of the solvent.

Unless otherwise defined, all technical and scientific terms used herein are accorded the meaning commonly known to one with ordinary skill in the art. All publications, patents, published patent applications, and other references mentioned herein are hereby incorporated by reference in their entirety.

ABBREVIATIONS

Abbreviations which may be used in the descriptions of the scheme and the examples that follow are:
Ac for acetyl;
AIBN for azobisisobutyronitrile;
$Bu_3SnH$ for tributyltin hydride;
CDI for carbonyldiimidazole;
dba for dibenzylidene acetone;
dppb for diphenylphosphino butane or 1,4-bis(diphenylphosphino)butane;
DBU for 1,8-diazabicyclo[5.4.0]undec-7-ene;
DEAD for diethylazodicarboxylate;
DMAP for dimethylaminopyridine;
DMF for dimethyl formamide;
DPPA for diphenylphosphoryl azide;
EtOAc for ethyl acetate;
HPLC for high-pressure liquid chromatography;
MeOH for methanol;
$NaN(TMS)_2$ for sodium bis(trimethylsilyl)amide;
NMMO for N-methylmorpholine N-oxide;
Rp for hydroxyl protecting group;
TEA for triethylamine;
THF for tetrahydrofuran;
TPP or $PPh_3$ for triphenylphosphine;
MOM for methoxymethyl;
Boc for t-butoxycarbonyl;
Bz for benzyl;
Ph for phenyl;
POPd for dihydrogen dichlorobis(di-tert-butylphosphinito-κP)palladate(II);
TBS for tert-butyl dimethylsilyl; or
TMS for trimethylsilyl.

All other abbreviations used herein, which are not specifically delineated above, shall be accorded the meaning which one of ordinary skill in the art would attach.

Synthetic Schemes

The present invention will be better understood in connection with Schemes 1-3. It will be readily apparent to one of ordinary skill in the art that the process of the present invention can be practiced by substitution of the appropriate reactants and that the order of the steps themselves can be varied.

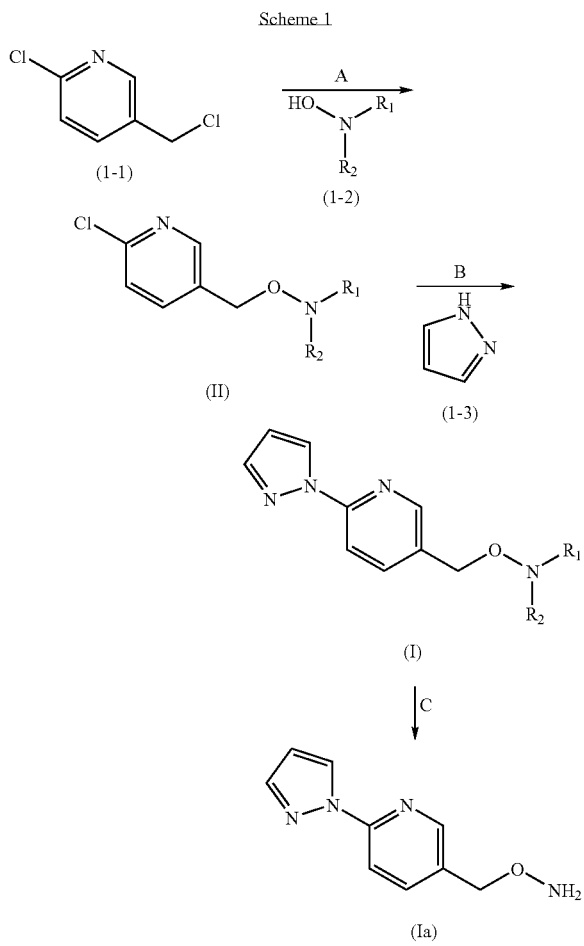

As outlined in Scheme 1, Step A, a compound of formula (II) is prepared by adding the compound of formula (1-2) to a compound of formula (1-1), wherein $R_1$ and $R_2$ are as previously defined. The present conversion preferably takes place in the presence of a base in an aprotic solvent.

A compound of formula (I) is prepared, as illustrated in Step B of Scheme 1, by reacting 2-chloro-5-methyl-hydroxyamine derivatives (II) with pyrazole in the presence of an acid catalyst in organic solvent, preferably in an aprotic solvent or without solvent, to provide a compound of the formula (I). In a preferred embodiment of the reaction, the reaction temperature is between 75° C. and 200° C. and the duration of the reaction is 6 to 48 hours. In a particularly preferred embodiment of the reaction, the acid is organic acid, such as acetic acid, toluene solufonic, methyl sulfonic acid, or camphorsulfonic acid without additional solvent.

In another embodiment of Scheme 1, a compound of formula (I) is prepared, as illustrated in Step B of Scheme 1, by reacting 2-chloro-5-methyl-hydroxyamine derivatives (II) with pyrazole in a neat organic acid, to provide a compound of the formula (I). In a preferred embodiment of the reaction, the reaction temperature is under a reflux temperature of the chosen acid, and the duration of the reaction is 12 to 48 hours. In a particularly preferred embodiment of the reaction, the acid is acetic acid, and the temperature is acetic acid reflux temperature.

In another embodiment of Scheme 1, a compound of formula (I) is prepared as illustrated in Step B, by reacting 2-chloro-5-methyl-hydroxyamine derivatives (II) with pyrazole in the presence of a base with catalyst, such as copper(I) salt or other transition metal derivatives combined with a 1,2-diamino derivatives, preferably in an aprotic solvent, to provide a compound of the formula (I). In a preferred embodiment of the reaction, the reaction temperature is between 25° C. and 150° C. and the duration of the reaction is less than 6 to 48 hours. In a particularly preferred embodiment of the reaction, the base is potassium carbonate and the aprotic solvent is neat pyrazole, the catalyst is copper(II) iodide and racemic-trans-N,N'-dimethylcyclohexane-1,2-diamine.

As outlined in Scheme 1, Step C, a compound of formula (Ia) is prepared by removal of the protecting group of $R_1$ and $R_2$ in the formula (I) under either basic or acidic conditions, depending on the nature of $R_1$ and $R_2$, wherein $R_1$ and $R_2$ are as previously defined.

Scheme 2 describes another process of preparing compounds I and Ia,

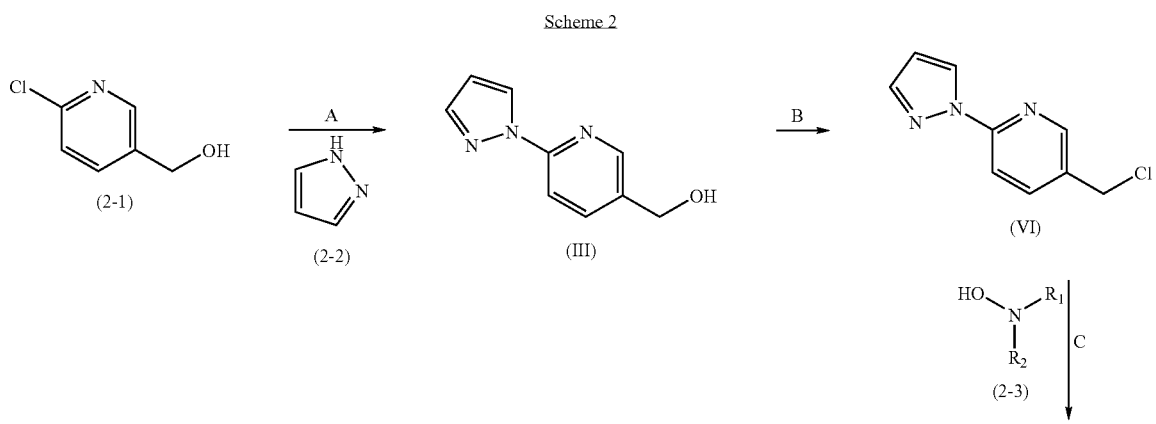

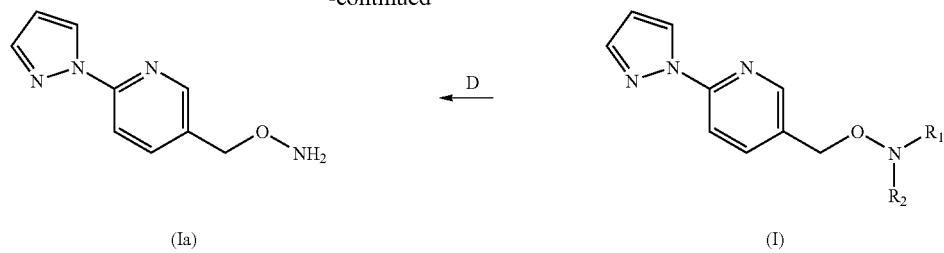

As outlined in Scheme 2, Step A, a compound of formula (III) is prepared by adding the compound of formula (2-2) to a compound of formula (2-1). The present conversion preferably takes place in the presence of acid catalyst or a basic catalytic system, in an aprotic solvent.

A compound of formula (III) is prepared, as illustrated in Step A of Scheme 1, by reacting 2-chloro-5-hydroxymethyl-pyridine (2-1) with pyrazole in the presence of acid catalyst in organic solvent, preferably in an aprotic solvent, to provide a compound of the formula (III). In a preferred embodiment of the reaction, the reaction temperature is between 75° C. and 200° C. and the duration of the reaction is 6 to 48 hours. In a particularly preferred embodiment of the reaction, the acid is organic acid, such as acetic acid, toluene solufonic, methyl sulfonic acid, or camphorsulfonic acid and the aprotic solvent is toluene.

Alternatively, a compound of formula (III) is prepared, as illustrated in Step A of Scheme 2, by reacting 2-chloro-6-hydroxymethyl-pyridine (2-1) with pyrazole in a neat organic acid, to provide a compound of the formula (III). In a preferred embodiment of the reaction, the reaction temperature is under a reflux temperature of the chosen acid, and the duration of the reaction is 12 to 48 hours. In a particularly preferred embodiment of the reaction, the acid is acetic acid, and the temperature is acetic acid reflux temperature.

Alternatively, a compound of formula (III) is prepared, as illustrated in Step A of Scheme 2, by reacting 2-chloro-5-hydroxymethyl-pyridine (2-1) with pyrazole in the presence of a base with catalyst, such as copper(I) salt or other transition metal derivatives combined with a 1,2-diamino derivatives, preferably in an aprotic solvent, to provide a compound of the formula (III). In a preferred embodiment of the reaction, the reaction temperature is between 25° C. and 150° C. and the duration of the reaction is less than 6 to 48 hours. In a particularly preferred embodiment of the reaction, the base is potassium carbonate and the aprotic solvent is neat pyrazole, the catalyst is copper(I) iodide and racemic-trans-N,N'-dimethylcyclohexane-1,2-diamine.

As outlined in Scheme 2, Step B, a compound of Formula (VI) is prepared by reacting of compound (III) with a chlorinating reagent.

A compound of formula (I) is prepared by adding a compound of formula (2-3), to a compound of formula (VI), as illustrated in Step C, wherein $R_1$ and $R_2$ are as previously defined. The present conversion preferably takes place in an aprotic solvent in the presence of a base.

A compound of formula Ia may be prepared from a compound of formula I as outlined in Scheme 1.

Scheme 3 describes an additional process of preparing compounds I and Ia.

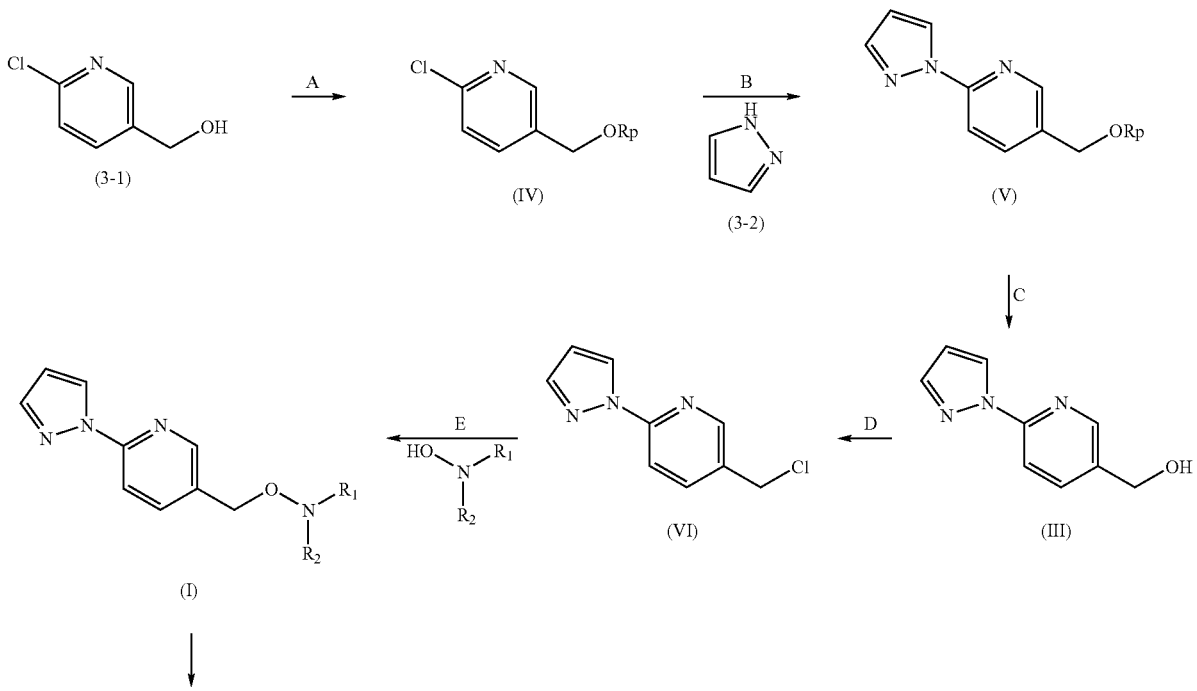

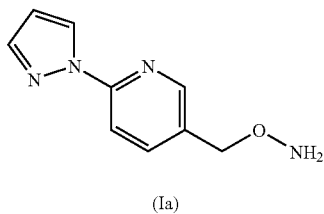

(Ia)

As illustrated in Scheme 3, Step A, a compound of formula (IV) is prepared by first reacting 2-chloro-5-hydroxymethyl-pyridine (3-1) with a hydroxyl protecting reagent Rp-X, wherein, Rp is previously defined and X is a leaving group, in the presence of a base, preferably in an aprotic solvent, to provide a compound of the formula (IV).

As outlined in Scheme 3, Step B, a compound of formula (V) is prepared by adding pyrazole to a compound of formula (IV). The present conversion preferably takes place in the same conditions as described in Scheme 2, Step A, with different starting material of formula (IV).

A compound of formula (III) is prepared, as illustrated in Step C of Scheme 3, by deprotecting the compound of formula (V) with acid or base in an aprotic organic solvent or an aqueous mixture thereof.

The compound of formula VI is prepared by reacting the compound of formula III with a chlorinating reagent. The compound of formula I is prepared from the compound of formula VI by reacting the compound of formula VI with at least one compound of formula $R_1R_2NOH$ wherein $R_1$ and $R_2$ are as previously defined, in the presence of base, optionally followed by hydrolysis to provide compounds of formula Ia.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Preparation of 2-chloro-5-pyridyl-N-methoxy succinimide (IIb)

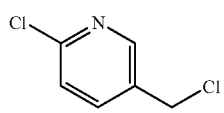

+

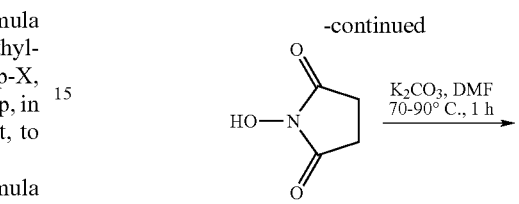

-continued

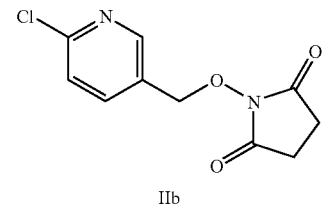
IIb

To a 5 L-three neck flask equipped with a mechanic stirrer, heating mantle with temperature controller and a gas outlet, were charged N-hydroxysuccinimide (426 g, 3.7 mol), 2-chloro-5-chloromethylpyridine (500 g, 3.1 mol) and anhydrous DMF (1 L). The mixture was stirred for 5 min when inner temperature dropped to 8.5° C. Anhydrous $K_2CO_3$ (640 g, 4.6 mol) was charged in one portion followed by anhydrous DMF (0.5 L). It was stirred for 5 min when inner temperature raised to 15.5° C. The mixture was heated to 70° C. (preset) within 30 min but the temperature continued to rise to 89° C. over 1 h of reaction period, during which a lot of gas was evolved and the reaction was finished as judged by MS and TLC, or simply the termination of gas-evolving. It was cooled down to room temperature, poured into water (6 L) with mechanic stirring. The insoluble was collected by filtration and washed with water (1.5 L), air-dried for 60 h to give the desired product as an off-white powder (364 g, 49%). ESIMS m/e (M+H)$^+$: 241. $^1$H NMR (500 MHz, CDCl$_3$): 8.44 (s, 1H), 7.95 (d, 1H, $^3$J=8.5 Hz), 7.41 (d, 1H, $^3$J=8.0 Hz), 5.14 (s, 2H), 2.73 (s, 4H) ppm. $^{13}$C NMR (125 MHz, CDCl$_3$): δ 170.8, 152.6, 150.2, 140.2, 128.2, 124.4, 74.9, 25.4.

Example 2

Preparation of 2-chloro-5-pyridyl-N-methoxy acetonimide (IIc)

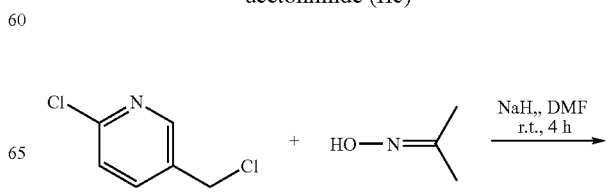

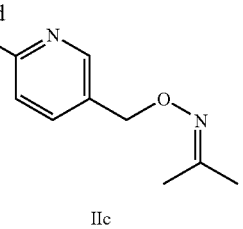

IIc

Sodium hydride (60 wt %, 485 mg, 12 mmol, 1.2 eq) was added portion-wise to a DMF (6 ml) solution of propan-2-one oxime (886 mg, 12 mmol, 1.2 eq). To the resulting white foaming suspension was added a DMF (3.5 ml) solution of 2-chloro-5-chloromethyl-pyridine (1.64 g, 10 mmol). After stirring for 4 hours at room temperature, the reaction mixture was diluted with 30 ml ethyl acetate. The organic solution was washed with water (3×50 ml), dried over sodium sulfate and concentrated. Column chromatography (hexanes) of the residue afforded the product as a light yellow oil 1.8 g (yield: 90%). MS-ESI m/z 198.98 (M+H)$^+$; $^1$H NMR (CDCl$_3$) δ 8.39 (s, 1H), 7.67 (d, 1H), 7.33 (d, 1H), 5.05 (s, 2H), 1.92 (s, 3H), 1.90 (s, 3H) ppm.

Example 3

Preparation of 2-(1-pyrazolyl)-5-pyridyl-N-methoxy succinimide (Ib)

Procedure-1

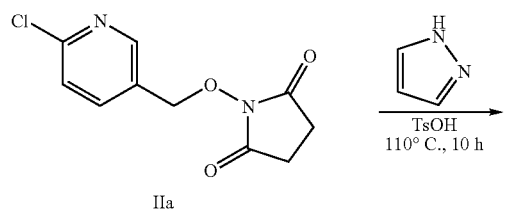

Starting material (IIa, 2.4 g, 10 mmol) and pyrazole (2.0 g, 29.4 mmol, 2.9 eq) were mixed with p-toluenesulfonic acid (190 mg, 1.0 mmol, 10 mol %). The resulting mixture was heated to 110° C. stirred for 10 hours. After cooling down, the residue was dissolved in CH$_2$Cl$_2$ (150 ml) and washed with half saturated aqueous sodium bicarbonate (50 ml). The organic phase was separated, dried over sodium sulfate and concentrated. Crystallization (CH$_2$Cl$_2$:hexanes, 1:2, 100 ml) afforded the product as a white crystalline solid 2.4 g (yield: 89%, purity>95% by $^1$H NMR). MS-ESI m/z 273.08 (M+H)$^+$; $^1$H NMR (CDCl$_3$) δ 8.58 (s, 1H), 8.46 (s, 1H), 8.03 (s, 2H), 7.76 (s, 1H), 6.45 (s, 1H), 5.18 (s, 2H), 2.68 (s, 4H) ppm, $^{13}$C NMR (CDCl$_3$) δ 171.2, 149.4, 142.7, 140.7, 127.5, 127.0, 112.5, 108.3, 75.7, 25.7 ppm.

Example 4

Preparation of 2-(1-pyrazolyl)-5-pyridyl-N-methoxy succinimide (Ib)

Procedure-2

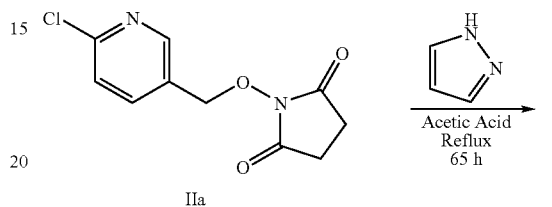

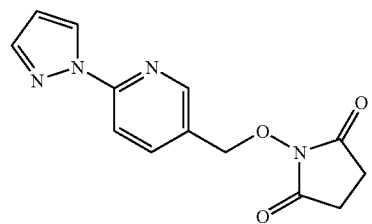

Ib

Starting material (224 mg, 0.93 mmol), pyrazole (74.5 mg, 1.09 mmol) were dissolved in acetic acid (1.4 ml) and stirred at 105° C. for 65 hours. After cooling down, the mixture was diluted with 10 ml ethyl acetate and carefully basified with saturated aqueous sodium bicarbonate solution to pH 8-9. The organic phase was separated, dried over sodium sulfate and concentrated. Column chromatography (EtOAc:hexanes, 1:1) of the residue afforded the product as an off-white solid 203 mg (yield: 80%). MS-ESI m/z 273.08 (M+H)$^+$; $^1$H NMR (CDCl$_3$) δ 8.58 (s, 1H), 8.46 (s, 1H), 8.03 (s, 2H), 7.76 (s, 1H), 6.45 (s, 1H), 5.18 (s, 2H), 2.68 (s, 4H) ppm, $^{13}$C NMR (CDCl$_3$) δ 171.2, 149.4, 142.7, 140.7, 127.5, 127.0, 112.5, 108.3, 75.7, 25.7 ppm.

Example 5

Preparation of 2-(1-pyrazolyl)-5-pyridyl-N-methoxy acetonimide (Ic)

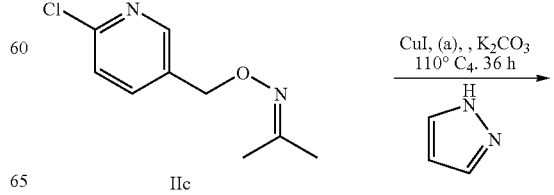

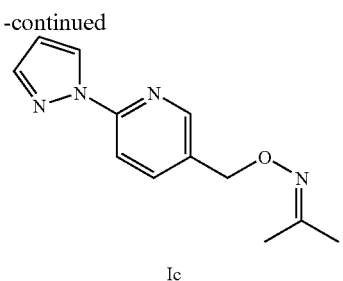

Ic a = [trans-cyclohexane-1,2-diyl with two NH groups]

Copper(I) iodide (30 mg, 0.16 mmol, 13 mol %), pyrazole (290 mg, 4.26 mmol, 3.5 eq), potassium carbonate (496 mg, 3.60 mmol, 3.0 eq), starting material (240 mg, 1.20 mmol) and rac-trans-N,N'-dimethylcyclohexane-1,2-diamine (65 mg, 0.46 mmol, 38 mol %) were mixed together and stirred at 110° C. for 36 hours. After cooling down, the mixture was dissolved in ethyl acetate and water (1:1, v/v, 10 ml). The organic phase was separated, dried over sodium sulfate and concentrated. Column chromatography (EtOAc:hexanes, 1:1) of the residue afforded the product as a light brown oil 220 mg (yield: 80%). MS-ESI m/z 231.05 (M+H$^+$.

Example 6

Preparation of (6-Pyrazol-1-yl-pyridin-3-yl)-methanol (III)

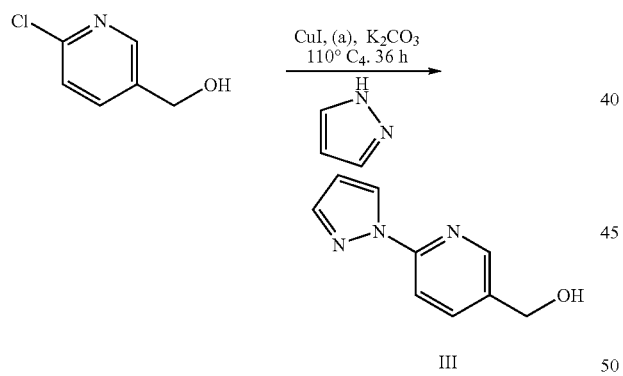

a = [trans-cyclohexane-1,2-diyl with two NH groups]

Copper(I) iodide (65 mg, 0.34 mmol, 22 mol %), pyrazole (411 mg, 6.04 mmol, 3.8 eq), potassium carbonate (705 mg, 5.10 mmol, 3.2 eq), (6-Chloro-pyridin-3-yl)-methanol (227 mg, 1.58 mmol) and rac-trans-N,N'-dimethylcyclohexane-1,2-diamine (92 mg, 0.65 mmol, 41 mol %) were mixed together and stirred at 110° C. for 44 hours. After cooling down, the mixture was dissolved in ethyl acetate and water (1:1, v/v, 10 ml). The organic phase was separated, dried over sodium sulfate and concentrated. Column chromatography (EtOAc:hexanes, 1:1) of the residue afforded the product as a light brown oil 292 mg (corrected yield: 95%), which was good for the next reaction although containing 10 wt % pyrazole by $^1$H NMR. MS-ESI m/z 175.97 (M+H)$^+$; $^1$H NMR (CDCl$_3$) δ 8.58 (s, 1H), 8.39 (s, 1H), 7.95 (d, 1H), 7.84 (d, 1H), 7.73 (s, 1H), 6.46 (s, 1H), 3.74 (s, 2H) ppm.

Example 7

Preparation of 5-Chloromethyl-2-pyrazol-1-yl-pyridine (IV)

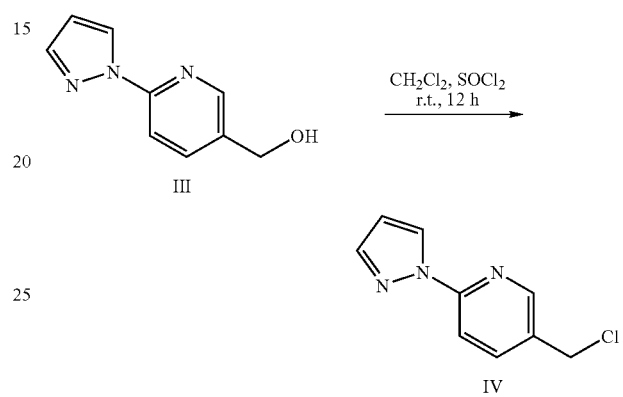

To a solution of alcohol (III) (10.5 g, 59.9 mmol) in CH$_2$Cl$_2$ (150 ml), SOCl$_2$ (36 g, 22 ml, 299.6 mmol) was added and the resulting reaction mixture was stirred at room temperature for a period of between 12 to 18 hours. The excess SOCl$_2$ was quenched with saturated aqueous NaHCO$_3$. The resulting mixture was extracted with CH$_2$Cl$_2$ and washed with brine. Removal of solvent gave a compound of formulae (11.15 g, 95% yield) as a white solid. MS-ESI=194.06, 196.06, $^1$H NMR (ppm): 8.59 (H3', d), 8.43 (H6, d), 8.03 (H2, d), 7.89 (H3, dd), 7.78 (H5', s), 6.50 (H4', t), 4.65 (—CH2-).

Example 8

Preparation of 2-(1-pyrazolyl)-5-pyridyl-N-methoxy succinimide (Ib) via 5-Chloromethyl-2-pyrazol-1-yl-pyridine (IV)

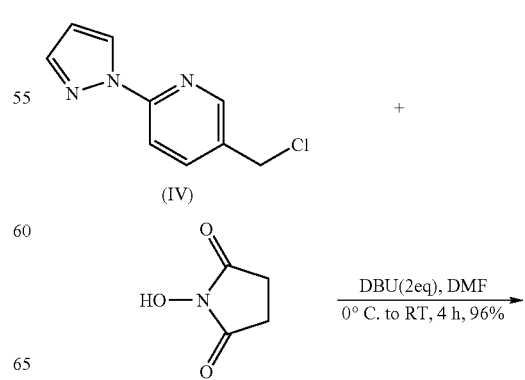

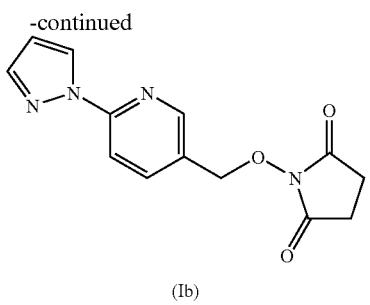
(Ib)

DBU (1.55 mL, 10.36 mmol) was added to a solution of N-hydroxysuccinimide (894 mg, 7.77 mmol) in 26 mL of DMF at 0° C. and stirred for 10 min followed by the addition chlorinated pyrazole-pyridine (compound IV, 1 g, 5.18 mmol). The reaction mixture was stirred for 4 hrs at room temperature. The resulting mixture was diluted with EtOAc; washed with saturated aqueous NaHCO$_3$ and brine. The combined organic layers dried over Na$_2$SO$_4$, filtered and evaporated in vacuo to yield 1.36 g (96%) of compound (Ib) as off-white powder. MS-ESI m/z 273.08 (M+H)$^+$; $^1$H NMR (CDCl$_3$) δ 8.58 (s, 1H), 8.46 (s, 1H), 8.03 (s, 2H), 7.76 (s, 1H), 6.45 (s, 1H), 5.18 (s, 2H), 2.68 (s, 4H) ppm, $^{13}$C NMR (CDCl$_3$) δ 171.2, 149.4, 142.7, 140.7, 127.5, 127.0, 112.5, 108.3, 75.7, 25.7 ppm.

The compound (Ib) can also be prepared according to the experimental procedure described in example 1.

Example 9

Preparation of 2-(1-pyrazolyl)-5-pyridyl-N-methoxy acetonimide (Ic)

The experimental procedure is similar to the procedure described in example 2. MS-ESI m/z 231.05 (M+H)$^+$.

Example 10

Preparation of O-(6-Pyrazol-1-yl-pyridin-3-ylmethyl)-hydroxylamine (Ia) via 2-(1-pyrazolyl)-5-pyridyl-N-methoxy succinimide (Ib)

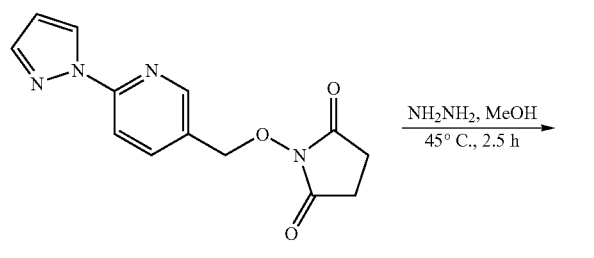

Starting material (2.0 kg, 7.3 mol) was dissolved in methanol (30 L). Hydrazine monohydrate (0.72 L, 14.9 mol, 2.0 eq) was added and the reaction mixture was stirred at 45° C. for 2.5 hours. After cooling down, the reaction mixture was diluted with water (8 L) and then was extracted with IPAC (3×8 L). The organic phase was combined, washed with half saturated aqueous sodium bicarbonate and concentrated. Crystallization (IPAC:heptane, 3:4, 7 L) afforded the product was a white crystalline solid (yield: 84%). MS-ESI m/z 191.09 (M+H)$^+$; $^1$H NMR (CDCl$_3$) δ 8.56 (d, 1H), 8.39 (d, 1H), 7.98 (d, 2H), 7.83 (dd, 1H), 7.74 (d, 1H), 6.47 (dd, 1H), 5.48 (s, 2H), 4.70 (s, 2H) ppm; $^{13}$C NMR(CDCl$_3$) δ 151.4, 148.4, 142.3, 139.3, 131.1, 127.3, 112.2, 108.1, 74.8 ppm.

Although the invention has been described in detail with respect to various preferred embodiments it is not intended to be limited thereto, but rather those skilled in the art will recognize that variations and modifications may be made therein which are within the spirit of the invention and the scope of the appended claims.

What is claimed is:

1. A process for preparing a compound of formula (I):

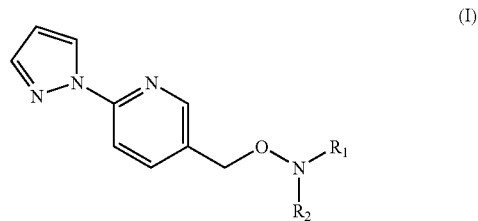
(I)

wherein R$_1$ and R$_2$ are each independently selected from:
(a) hydrogen; and
(b) NH$_2$;
or one of R$_1$ or R$_2$ is hydrogen and the other is selected from:
(a) C(O)R$_3$, where R$_3$ is C$_1$-C$_6$ alkyl, optionally substituted with one or more substituents selected from aryl, substituted aryl, heteroaryl, or substituted heteroaryl;
(b) C(O)OR$_3$, where R$_3$ is as previously defined; and
(c)

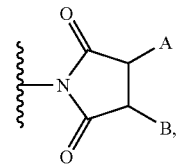

wherein A and B are each independently hydrogen, a substituted or unsubstituted aliphatic group, a substituted or unsubstituted cyclic group, a substituted or unsubstituted heterocyclic group, a substituted or unsubstituted aryl group, a substituted or unsubstituted alicyclic group, or a substituted or unsubstituted heteroaryl group or A and B taken together with the carbon to which they are attached form a cyclic moiety selected from: aryl, substituted aryl, heterocyclic, substituted heterocyclic, alicyclic, or substituted alicyclic alternatively, R$_1$ and R$_2$ are taken together with the nitrogen atom to which they are attached to form N═C(R$_4$)(R$_5$), where R$_4$ and R$_5$ are each independently selected from a substituted or unsubstituted aliphatic group, a substituted or unsubstituted cyclic group, a substituted or unsubstituted heterocyclic group, a substituted or unsubstituted aryl group, a substituted or unsubstituted alicyclic group, or a substituted or unsubstituted heteroaryl group;
said process comprising:
(1) reacting pyrazole with (6-chloro-pyridin-3-yl)-methanol in the presence of:
(a) an acid catalyst;
(b) a neat organic acid; or
(c) a transition metal catalyst and base;
to form a compound of formula III

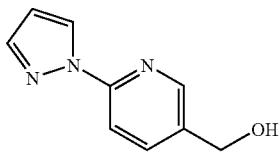

(2) halogenating the compound of formula III with a chlorinating reagent to provide a compound of formula (VI):

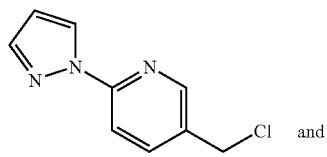

(VI)

and (3) reacting a compound of the formula $R_1R_2NOH$, with the compound of formula VI to form a compound of formula I:

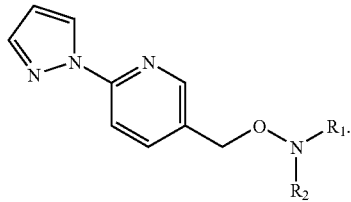

(I)

2. The process of claim 1 further comprising the step of hydrolyzing the compound of formula I wherein at least one of $R_1$ and $R_2$ is not hydrogen with a base or an acid in a protogenic organic solvent or aqueous solution, to yield a compound of formula (Ia), O-(6-Pyrazol-1-yl-pyridin-3-yl-methyl)-hydroxylamine.

3. The process of claim 1, wherein step 1 comprises reacting pyrazole with (6-Chloro-pyridin-3-yl)-methanol in the presence of toluene sulfonic acid to provide (6-Pyrazol-1-yl-pyridin-3-yl)-methanol.

4. The process of claim 1, wherein step 1 comprises reacting pyrazole with (6-Chloro-pyridin-3-yl)-methanol in acetic acid to provide (6-Pyrazol-1-yl-pyridin-3-yl)-methanol.

5. The process of claim 1, wherein step 1 comprises reacting pyrazole with (6-Chloro-pyridin-3-yl)-methanol in the presence of CuI and trans-N,N'-dimethylcyclohexane-1,2-diamine to provide (6-Pyrazol-1-yl-pyridin-3-yl)-methanol.

6. The process of claim 1, wherein step 2 comprises reacting thionyl chloride with (6-Pyrazol-1-yl-pyridin-3-yl)-methanol to provide 5-Chloromethyl-2-pyrazol-1-yl-pyridine.

7. The process of claim 1, wherein step 3 comprises reacting N-hydroxysuccinimide with 5-Chloromethyl-2-pyrazol-1-yl-pyridine in the presence of DBU to provide 2-(1-pyrazolyl)-5-pyridyl-N-methoxy succinimide.

8. The process of claim 1, wherein step 3 comprises reacting propan-2-one oxime with 5-Chloromethyl-2-pyrazol-1-yl-pyridine in the presence of sodium hydride to provide 2-(1-pyrazolyl)-5-pyridyl-N-methoxy acetonimide.

9. The process of claim 2 comprising reacting hydrazine with 2-(1-pyrazolyl)-5-pyridyl-N-methoxy succinimide in methanol to provide O-(6-Pyrazol-1-yl-pyridin-3-ylmethyl)-hydroxylamine.

10. The process of claim 2 comprising reacting sulfuric acid with 2-(1-pyrazolyl)-5-pyridyl-N-methoxy acetonimide in methanol to provide O-(6-Pyrazol-1-yl-pyridin-3-ylmethyl)-hydroxylamine.

* * * * *

UNITED STATES PATENT AND TRADEMARK OFFICE
CERTIFICATE OF CORRECTION

| | | |
|---|---|---|
| PATENT NO. | : 7,919,627 B2 | Page 1 of 1 |
| APPLICATION NO. | : 12/135299 | |
| DATED | : April 5, 2011 | |
| INVENTOR(S) | : Tang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 53 days.

Signed and Sealed this
Twenty-first Day of June, 2011

David J. Kappos
*Director of the United States Patent and Trademark Office*